United States Patent
Acher et al.

(10) Patent No.: US 8,444,708 B2
(45) Date of Patent: *May 21, 2013

(54) EPILATORY COMPOSITIONS

(75) Inventors: David Acher, Hull (GB); Frederic De La Torre, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,924

(22) Filed: May 3, 2011

(65) Prior Publication Data

US 2011/0203055 A1  Aug. 25, 2011

Related U.S. Application Data

(63) Continuation of application No. 10/502,868, filed as application No. PCT/GB03/00648 on Feb. 12, 2003, now abandoned.

(30) Foreign Application Priority Data

Feb. 13, 2002 (GB) .................................. 0203396.7

(51) Int. Cl.
  *C14C 1/06* (2006.01)
(52) U.S. Cl.
  USPC ............................................................ 8/160

(58) Field of Classification Search
  USPC ............................................................. 8/160
  See application file for complete search history.

(56) References Cited

U.S. PATENT DOCUMENTS 3,981,681 A * 9/1976 de la Guardia .................. 8/161
4,282,877 A * 8/1981 Mathews ...................... 606/134

FOREIGN PATENT DOCUMENTS

GB  2336535  * 10/1999

OTHER PUBLICATIONS

Ehlers et al, Females have lower skin surface pH than men, May 2001, Skin Research and Technology, vol. 7, Issue 2, 1 page (abstract).*
Davis, Tinsley, Re: How does the pH of the skin serve as a barrier against bacteria?, Apr. 8, 1999, MadSci Network, 1 page.*

* cited by examiner

*Primary Examiner* — Daniel Sullivan
*Assistant Examiner* — Trevor Love
(74) *Attorney, Agent, or Firm* — Norris McLaughlin & Marcus PA

(57) ABSTRACT

An epilatory composition of the adhesive type comprises a gel-like matrix material, for example of a rosin-based or sugar-based material, together with 0.1-5 wt % of a branched polyalkene, for example polyisobutene. The resulting compositions offer skin care benefits while maintaining excellent viscoelastic and adhesive properties.

4 Claims, No Drawings

EPILATORY COMPOSITIONS

The present application is a Continuation application of U.S. Ser. No. 10/502,868, which in turn was an application filed under 35 USC 371 of PCT/GB03/00648.

Epilatory compositions formed of viscoelastic materials are well known. The viscoelastic materials may in certain embodiments be rosinous materials. In other embodiments they may be sugar-based.

In some products the epilatory compositions may be supplied in the form of strips, retained between cellophane sheets. The cellophane sheets may have coatings of polyvinyl chloride, which acts as a barrier preventing the composition, or components of it, from migrating through the sheets; and also having the correct adhesive properties for use. In use, the user peels away one of the cellophane sheets, presses the epilatory strip firmly onto the area to be plucked, then pulls one end of the remaining cellophane sheet sharply away from the area. The hairs trapped in the composition are removed from the treated area along with, optimally, all of the composition, still attached to the remaining backing strip.

In an alternative approach a composition may be warmed, and then applied to the skin by means of a spatula or other applicator. Strips of fabric are then applied so that they adhere to the epilatory composition. The strips are then pulled sharply to remove the epilatory material, and hair, from the skin.

The rosinous materials have excellent viscoelastic properties for epilatory compositions of the type described above but may irritate the skin of some users, if they fail to follow the instructions given.

It would be desirable to locate an ingredient which is beneficial in terms of skin care, but which does not compromise to any significant degree the viscoelastic and the adhesive properties of epilatory compositions, whether rosinous or sugar-based.

In accordance with a first aspect of the present invention there is provided an epilatory composition comprising a matrix material of the adhesive type, wherein the composition includes a branched polyalkene.

The matrix material may comprise a tackifying polymeric material, for example a tackifying aliphatic or aromatic resin.

The matrix material may comprise a sugar-based material. Examples of specifications describing epilatory compositions based on heating sugar(s) with acids (such as citric acid) are disclosed in GB 901624, GB 1242083, GB 2231494A, and GB 2157951A.

The matrix material may comprise a rosinous material, for example a rosin ester and/or colophony.

The branched polyalkene is suitably a polyalkene having $C_{1-4}$ alkyl groups, preferably methyl groups, projecting from a carbon backbone. Preferably the branched polyalkene comprises units derived from isobutene. These may have been homopolymerised, to form polyisobutene, or may have been copolymerised with other unsaturated materials, preferably other alkenes.

Most preferably the branched polyalkene used is fully saturated. Depending on the manufacturing process this may mean that it has been hydrogenated.

The branched polyalkene may be regarded as a polymer having a carbon backbone carrying a proportion of pendent alkyl groups, preferably methyl groups. Preferably the carbon backbone carries both hydrogen atoms and pendent groups. The numerical ratio of pendent alkyl groups to hydrogen atoms on the backbone is suitably in the range 0.1:1-10:1, preferably 0.5:1-3:1, and most preferably 0.8:1-1.2:1 (such hydrogen atoms are directly on the backbone; hydrogen atoms within the pendent alkyl groups are not included). Especially preferred is a ratio of substantially 1:1, as is obtained with homopolymeric isobutene.

A preferred material is hydrogenated polyisobutene, a readily available material currently used in cosmetics. Grades are available under the trade marks POLYSYNLANE and PARLEAM, from Rossow Cosmetiques, France, or Nof Corporation, Japan.

An especially preferred material is non-hydrogenated polyisobutene, a readily available material currently used in cosmetics. Grades are available under the trade mark INDOPOL, from BP Chemicals, UK.

Suitably the branched polyalkene provides up to 20% of the total weight of the composition, preferably up to 15%, more preferably up to 10%, and most preferably up to 5%. Especially preferred is an amount up to 3% of the total weight of the composition.

Suitably the branched polyalkene provides at least 0.1% of the total weight of the composition, preferably at least 0.5%, most preferably at least 0.9%.

Suitably the branched polyalkene has a weight average molecular weight in the range 1,000 to 100,000, preferably 3,000 to 30,000.

Suitably the branched polyalkene is in the nature of a highly viscous liquid.

Preferably the branched polyalkylene is in the nature of a waxy or tacky solid or semi-solid.

We have found that the inclusion of a branched polyalkylene in an epilatory composition of the adhesive type produces a valuable skin care benefit, even when present in a small amount. The benefit is such that the irritation which certain epilatory compositions can elicit in some users is eased, or avoided altogether. Excellent adhesive and viscoelastic properties are also achieved.

The matrix material may comprise a sugar-based material and a rosinous material in admixture. The following paragraphs further define such mixtures.

Suitably, the epilatory composition of the present invention comprises greater than or equal to 70% by wt, preferably greater than or equal to 75% by wt, preferably greater than or equal to 80% by wt, preferably greater than or equal to 82% wt of sugar-based material.

Suitably, the epilatory composition of the present invention comprises less than or equal to 95% by wt, preferably less than or equal to 92.5% by wt, preferably less than or equal to 90% by wt, more preferably less than 90% by wt, more preferably less than or equal to 88% by wt of sugar-based material.

Suitably, the epilatory composition of the present invention comprises greater than or equal to 5% by wt, preferably greater than or equal to 7.5% by wt, preferably greater than or equal to 10% by wt, more preferably greater than 10% by wt, most preferably greater than or equal to 12% by wt of rosinous material.

Suitably, the epilatory composition of the present invention comprises less than or equal to 30% by wt, preferably less than or equal to 25 by wt, preferably less than or equal to 20% by wt, most preferably less than or equal to 18% by wt of rosinous material.

A particularly preferred epilatory composition of the present invention comprises greater than 10% by wt and less than 30% by wt, especially greater than or equal to 12% by wt and less than or equal to 20% by wt, of rosinous material.

Unexpectedly, it has been found that by including a rosinous material in the epilatory compositions of the present invention within the aforementioned defined limits then the adhesive properties of the sugar-based composition may be significantly enhanced while maintaining the water rinsability characteristics of the sugar-based composition.

Suitably, the weight ratio of sugar-based material to rosinous material in the epilatory composition of the present invention is less than or equal to 19:1, preferably less than or equal to 15:1, preferably less than or equal to 13:1, preferably less than or equal to 10:1, preferably less than or equal to 9:1, most preferably less than or equal to 7.5:1.

Suitably, the weight ratio of sugar-based material to rosinous material in the epilatory composition of the present invention is greater than or equal to 2.3:1, preferably greater than or equal to 3:1, more preferably greater than or equal to 4:1, most preferably greater than or equal to 5:1.

A particularly preferred epilatory composition of the present invention comprises a weight ratio of sugar-based material to rosinous material of less than 9:1 and greater than or equal to 2.3:1, especially less than or equal to 7.5:1 and greater than or equal to 4:1.

Preferably, the rosinous material is in the form of droplets, which may be of any shape, dispersed within the matrix material. Typically, the droplets are spherical and/or ellipsoidal in shape.

Suitably, the average maximum cross-sectional dimension of the droplets of rosinous material, as measured by photon correlation spectroscopy, is greater than or equal to 20 nm, more preferably greater than or equal to 30 nm, most preferably greater than or equal to 40 nm, especially greater than or equal to 50 nm.

Suitably, the average maximum cross-sectional dimension of the droplets of rosinous material, as measured by photon correlation spectroscopy, is less than or equal to 5000 nm, preferably less than or equal to 1500 nm, preferably less than or equal to 1000 nm, most preferably less than or equal to 500 nm.

Preferably the epilatory composition comprises at least 60% wt/wt of the matrix material, for example rosinous material and/or sugar-based material, preferably at least 70% wt/wt, more preferably at least 80% wt/wt.

Preferably the epilatory composition is a so-called "cold" epilatory composition (that is, one which can be applied at ambient temperature without reheating).

Preferably the epilatory composition comprises a particulate material in admixture with the matrix material. Preferably the particulate material is a colloidal material. Preferably it has particles of mean diameter 1-200 nm, more preferably 5-100 nm, and most preferably 10-50 nm.

Preferably the particles, when present in the epilatory composition, are in an amount of at least 1% wt on total weight of composition, more preferably at least 2%, and most preferably at least 3%. Suitably they are present in an amount up to 20% on total weight of composition, and preferably up to 10%.

Preferred particulate materials for use in the present invention are siliceous materials. Especially preferred is fumed silica.

Fumed silica is currently manufactured in a process that involves flame hydrolysis of silicon tetrachloride, in an oxy-hydrogen flame. It is a colloidal form of silica having silanol groups, able to participate in hydrogen bonding. Fumed silica typically comprises colloidal particles of mean diameter 1-200 nm. Preferably the fumed silica is of mean diameter 5-100 nm, more preferably 10-50 nm. The external surface area is typically in the range 15-380 $m^2/g$. Fumed silicas are typically non-porous and thus have no internal surface area. They may be hydrophobic and of use in the present invention but preferred fumed silicas for use in the present invention are hydrophilic.

The epilatory composition may suitably comprise up to 40%, preferably up to 20%, of other components, which may include one or more of a natural wax, a fragrance, a polymer, an essential oil, a silicone oil, a colorant, an anti-oxidant or a paraffin or mineral oil.

Preferably the epilatory composition is such that its elastic modulus exceeds its viscous modulus at all frequencies up to 0.1 rad/s at 50° C. Preferably the elastic modulus of the epilatory composition exceeds its viscous modulus at all frequencies up to 1 rad/s at 50° C., more preferably at all frequencies up to 2 rad/s at 50° C.

In certain embodiments, notably epilatory compositions having a sugar-based matrix material, the elastic modulus may exceed the viscous modulus at all frequencies up to 20 rad/s at 50° C.

Preferably at certain higher frequencies (representative of the rapid removal of the epilatory composition from the user's skin), the elastic modulus also exceeds the viscous modulus, at temperatures within the temperature range 20-50° C.

Preferably the elastic modulus exceeds the viscous modulus (when measured at 35° C.) at a frequency of at least 10,000 rad/s, more preferably at a frequency at least 5,000 rad/s.

Thus, preferably the epilatory composition is such that, at ambient temperatures, at low frequencies of applied stress the elastic modulus exceeds the viscous modulus; at high frequencies of applied stress the elastic modulus exceeds the viscous modulus; and at moderate frequencies, in between, the viscous modulus exceeds the elastic modulus. The epilatory composition in transit and storage corresponds to the low frequency condition, and the non-viscous nature of the composition aids shape stability in storage and transit; the application of the epilatory composition to the skin corresponds to the moderate frequency condition, and the viscous nature of the composition aids application and good contact with hair and skin; and pulling the epilatory composition sharply from the skin corresponds to the high frequency condition, the non-viscous, glassy nature of the composition aiding effective hair removal. The transition between the low frequency condition and the moderate frequency condition is known as the gel point. The transition between the moderate frequency condition and the high strain rate condition is known as the glass transition.

The elastic modulus G' (sometimes known as the storage modulus) corresponds to the energy which can be stored and released by a bulk material. The viscous modulus G" (sometimes known as the loss modulus) corresponds to the energy dissipated by a bulk material due to friction between its macromolecules when it is deformed.

$$G' = \frac{\sigma^\circ}{\gamma^\circ} \cos\delta$$

$$G'' = \frac{\sigma^\circ}{\gamma^\circ} \sin\delta$$

wherein $\sigma_o$ is the stress amplitude, $\gamma_o$ is the strain amplitude and $\delta$ is the out-of-phase coefficient.

The measurements quoted later are based on studies carried out into the rheology of the viscoelastic compositions in order to obtain a better understanding of their adhesive behaviour and their suitability as epilatory materials. These studies involved subjecting the materials to dynamic investigations in which a sinusoidal strain at defined frequencies was applied to the materials and the resulting output force was measured. In these studies a stress control rheometer was used, the SR rheometer commercially available from the company Rheometrics, using parallel plate geometry of 25 mm in diameter. The output force was found to include an in-phase elastic component G' and an out-of-phase viscous component G". The output force can be expressed as follows.

$$\sigma = \sigma\circ \sin(t\omega + \delta)$$
$$= \sigma\circ \cos\delta\sin t\omega + \sigma\circ \cos\delta\cos t\omega$$

where ω is the test frequency and t is the time.

Within the linear stress-strain domain of the material G' is desirably lower than G" at moderate frequency oscillation in order to prevent the material cracking and to ensure that the material has strong adhesion at the material/hair interface. The values of G' and G" at moderate frequency oscillation are a measure of how readily the material wets the hairs. Moderate frequency oscillation is a long time process and corresponds to the time when the material is being applied to the skin. The lower values of G' and G" at this moderate frequency, the better the material wets the hairs. Thus the hairs become well embedded in the material in a very short time (ie the time needed for spreading the material on the skin). However G' should be higher than G" at high frequency oscillation (which mimics the action of the user in rapidly pulling the strip from the body) in order to remove hairs efficiently. Also, at low frequency oscillation, or no oscillation, G' is preferably higher than G", in accordance with this invention, in order to obtain the benefit of enhanced stability, even when warm.

The definitions given herein refer to stresses applied to the material within its linear stress-strain domain, which may typically be up to a few thousand Pa.

Preferably, therefore, the composition is of an elastic nature when unstressed.

Preferably, therefore, the composition is of a viscous nature when moderately stressed, for example on application to the skin.

Preferably, therefore, the composition is of an elastic nature when highly stressed, for example on removal from the skin (as by abrupt pulling).

By ensuring that the epilatory composition satisfies the above parameters, it can be readily applied to the skin at body temperature, yet it is very efficient at removing hairs from the skin and, surprisingly, the user experiences less pain.

References in this specification to a material not under applied stress are to a material in the form of a flat sheet, resting on a horizontal surface.

If wished the epilatory composition of the present invention may be provided in a container, from which the user removes it using, for example, a spatula or an applicator fitted to the container, and applies it to the skin. A fabric can then be used to pull the applied material in one piece from the skin. Alternatively, and preferably, the epilatory composition is supplied in the form of strips, sandwiched between sheets, for example of cellophane, or paper or another non-woven material. In use, one sheet is removed from a strip of epilatory composition and that strip is then applied to the skin with the remaining sheet uppermost. The end of that sheet is grasped and pulled sharply, to remove the strip of epilatory composition from the skin, along with hairs with which it is in contact.

Preferably an epilatory composition of the invention is mildly acidic, for example having a pH in the range 4.5-6.5, preferably 5-6.

Preferred epilatory compositions of the present invention are such that residues are removable from the user's skin by normal water washing.

A preferred epilatory composition of the present invention comprises, in accordance with the definitions given previously:

at least 60% wt of a sugar-based matrix material;
0-30% wt of a rosin-based matrix material;
0.1-5% wt of a branched polyalkene;
1-20% wt of a particulate material; and
0-40% wt of additional components.

An especially preferred epilatory composition of the present invention comprises, in accordance with the definitions given previously:

at least 70% wt of a sugar-based matrix material;
2-20% wt of a rosin-based matrix material;
0.5-5% wt of a branched polyalkene;
1-5% wt of a particulate material; and
0-20% wt of additional components.

In accordance with further aspects there are provided a method of manufacturing an epilatory composition, as defined above; an epilatory product, for example a strip of such an epilatory composition or a dispenser containing such a composition, having an applicator to deposit a sheet thereof on the skin or a user; and a method of epilation, using such a composition or product.

The invention will now be further described, by way of example.

EXAMPLE 1

A composition was made with the following ingredients.

| Ingredients | % wt/wt |
|---|---|
| Inverted sugar base: | |
| Sugar (sucrose) | 78.3 |
| Citric acid monohydrate | 1.3 |
| DERMULSENE RA 405 | 1.5 |
| Water | 7.4 |
| DERTOLINE RC2 rosinous material | 7 |
| HDK N20 fumed silica | 2 |
| PARLEAM SV polyisobutene | 1 |
| KOH (50% in water) | 1.5 |

DERMULSENE RA 405 is a collophonium emulsion available from DRT-Granel.
DERTOLINE RC2 is a colophonium derived resin, available from DRT-Granel.
HDK N20 is a fumed silica powder available from Wacker.
PARLEAM SV, also called POLYSYNLANE SV, is an hydrogenated polyisobutene polymer available from Rossow Cosmetiques, France. The SV grade denotes the super high viscosity grade.
Method of Manufacture
1. Preparation of an Inverted Sugar-Based Material:
   a. Prepare an inverted sugar (sugar/citric acid/water)—cool down to 60° C. and maintain the tank temperature at 60° C. during the process;
   b. Add 1.5% of DERMULSENE RA 405 and mix slowly during 30 minutes;
   c. Adjust the viscosity of the mix to 130 Pa·s (at a reference temperature of 35° C.) by adding water.
2. Dispersion of Rosin and PARLEAM SV in the Sugar Base
   a. Add the PARLEAM SV previously preheated in the oven at 60° C., to the inverted sugar-based material from Step 1, and incorporate it by mixing;
   b. Then add the DERTOLINE RC2 previously preheated in the oven at 60° C. and incorporate it by mixing;

3. Formula Gelation
 a. Add the HDK N20 and homogenise using a high speed turbine at 10 rpm.
 b. Add the potassium hydroxide under stirring. The resulting composition at ambient temperature had the appearance of a viscous gel.
4. Formula Characterisation
 a. pH of the composition (dilute 50% in water)=5.6
 b. gel point at 35° C. (G'=G")=18 rad/s
 c. viscosity at 35° C.=210 Pa·s The resulting gel product could be formed in standard manner into water rinsable cold wax strips.

The composition is particularly suitable for sensitive skin. To this end, it is predominantly sugar-based; the rosinous material content is low (but sufficient to promote good performance); and it contains PARLEAM SV.

Preliminary tests indicate that the composition does not flow at high temperatures such as would be found during summer months in warm countries, and that other required properties are very good. The PARLEAM SV component appears not to have caused any adverse effect on the properties of the composition.

EXAMPLE 2

A composition was made with the following ingredients:

| Ingredients | % wt/wt |
| --- | --- |
| Inverted sugar base (same as Example 1) | 95.5 |
| HDK N20 | 2 |
| PARLEAM SV | 1 |
| KOH (50% in water) | 1.5 |

The sugar base and the PARLEAM SV were incorporated as described in Example 1.
The composition had the following properties:
pH (dilute 50% in water)=5.44
gel point at 35° C.=6.25 rad/s
viscosity at 35° C.=190 Pa·s.

EXAMPLE 3

A composition for manufacture into an epilatory strip was made with the following ingredients.

| Ingredients | % wt/wt |
| --- | --- |
| Inverted sugar base: | |
| Sugar (sucrose) | 77.6 |
| Citric acid monohydrate | 1.3 |
| DERMULSENE RA 405 | 1.3 |
| Water | 7.4 |
| TEG rosinate | 4.84 |
| DERTOLINE RC2 rosinous material | 2.16 |
| INDOPOL H2100 polyisobutene | 1 |
| KOH (50% in water) | 1.4 |

TEG rosinate is triethylene glycol rosinate available from DRT-Granel.

INDOPOL H2100 is non-hydrogenated polyisobutene, molecular weight approx. 2,000, available from BP. Being non-hydrogenated it has unsaturation at the polymer termini.

The epilatory composition was prepared by the method described in Example 1, except:

In Step 1 the temperature was 65° C.

In Step 2 both rosinates and the polyisobutene were pre-mixed in a separate tank and added to the inverted sugar material at 65° C. Homogenisation for 5 minutes using a high speed turbine operated at 1,000 rpm ensured good dispersion of the rosinates.

In Step 3a. the fumed silica was blended in using a high speed rotor/stator mixer/pump operated at 1,000 rpm for 15 minutes.

In Step 3b. the KOH was added in a single addition with stirring. The composition was then recirculated in the high speed rotor/stator mixer/pump. Friction increased the temperature to 80° C.

The gel point of the Example 3 composition, measured at 50° C., is 25 rad/s. Its viscosity, measured at 35° C., is 230 Pa·s. Its pH is 5.5.

The invention claimed is:
1. An epilatory composition comprising:
 at least 70% wt of a sugar-based matrix material;
 2-20% wt of a rosin-based matrix material;
 0.5-3% wt of a branched polyalkene;
 1-5% wt of a particulate material; and
 0-20% wt of additional components, wherein the composition has an elastic modulus that exceeds a viscous modulus of the matrix material (i) at all frequencies up to 20 rad/s at 50° C. and (ii) at a frequency of at least 5,000 rad/s at 35° C., wherein the composition has a pH of 5-6.
2. An epilatory product comprising an epilatory composition according to claim 1, the product being selected from: strips of such a composition sandwiched between sheets which are peelable from the strips; and a dispenser containing such a composition, having an applicator adapted to deposit a sheet thereof on the skin of a user.
3. An epilatory composition according to claim 1, wherein the epilatory composition is a gel.
4. An epilatory composition according to claim 1, wherein the particulate material is present at a concentration greater than 1% wt. and less than 5% wt.

* * * * *